United States Patent [19]

Takahashi et al.

[11] 4,274,745
[45] Jun. 23, 1981

[54] METHOD AND APPARATUS FOR DETECTING FOREIGN MATTERS IN LIQUIDS

[75] Inventors: Toshio Takahashi, Honjo; Ryosaku Tagaya, Isesaki, both of Japan

[73] Assignee: Eisai Co., Ltd., Tokyo, Japan

[21] Appl. No.: 900,350

[22] Filed: Apr. 27, 1978

[30] Foreign Application Priority Data

May 12, 1977 [JP] Japan .................................. 52-54607
Feb. 1, 1978 [JP] Japan .................................. 53-10685

[51] Int. Cl.³ ........................................... G01N 21/24
[52] U.S. Cl. .................................. 356/427; 250/574; 356/240
[58] Field of Search ...................... 356/240, 427, 441; 250/223 B, 573, 574, 576

[56] References Cited

U.S. PATENT DOCUMENTS

| | | | |
|---|---|---|---|
| 3,900,266 | 8/1975 | Takahashi et al. | 356/427 |
| 3,966,332 | 6/1976 | Knapp et al. | 356/240 |
| 4,028,553 | 6/1977 | Farcinade | 250/573 |
| 4,058,737 | 11/1977 | Takahashi et al. | 250/573 |
| 4,095,904 | 6/1978 | Klein et al. | 356/427 |

FOREIGN PATENT DOCUMENTS

1082928 9/1967 United Kingdom ...................... 356/240
1147838 4/1969 United Kingdom ...................... 356/240

Primary Examiner—R. A. Rosenberger
Attorney, Agent, or Firm—Blanchard, Flynn, Thiel, Boutell & Tanis

[57] ABSTRACT

Method and apparatus for detecting foreign matters in liquids comprising the steps of turning at a high speed a transparent container filled with a liquid, bringing the container to a standstill quickly permitting suspended foreign matters to swirl with the liquid, illuminating the liquid and foreign matters causing the transmitted light to be received by a light detector consisting of a multiplicity of small light sensitive elements measuring 0.01 mm²–1 mm² and capable of providing output signals proportional to the projected area of foreign matters, and rejecting defective containers that give output signals exceeding the reference value. The small light sensitive elements are connected to the detection visual field selector circuits so that the detection visual field can be changed by selecting a proper number of the small light sensitive elements to be employed according to the size of object to be detected.

3 Claims, 9 Drawing Figures

METHOD AND APPARATUS FOR DETECTING FOREIGN MATTERS IN LIQUIDS

BACKGROUND OF THE INVENTION

The present invention relates to a method and apparatus for detecting foreign matters that might be present in liquids. More particularly, the present invention relates to a method and apparatus for detecting undesirable small foreign matters that might be present in medical fluids filled in transparent containers such as injection ampoules and vials, which often contain foreign matters like glass chips, small particles, and fibers. The presence of such foreign matters is not desirable for quality, and it is necessary to select defective containers containing foreign matters by testing all the containers filled with medical fluids.

In a conventional method the detection of foreign matters is accomplished as follows: An ampoule to be tested is turned at a high speed and then brought to a standstill quickly. The suspended foreign matters that swirl together with the liquid in the ampoule are illuminated. The beam of light which has passed through the liquid is received by a light detector, and a decrease in light received is regarded as an indication of the presence of foreign matters. In such a method it was difficult to detect foreign matters sensitively with a single photoelectric element as a light detector, because foreign matters to be detected are extremely small as compared with the detection visual field and the difference of photocurrent caused by the presence of foreign matters is also extremely small. Another conventional method in which is used a light detector consisting of many small light sensitive elements equivalent in size to foreign matters and outputs of respective light sensitive elements are scanned, has a fatal drawback that complex electric circuits are required for signal processing and the result of detection is affected by the shape of foreign matters.

In the case of the small light sensitive elements having a light sensitive area equal to or smaller than the projected area of the minimum size of foreign matter particles, sensitive detection can be accomplished because the light sensitive surface is shaded by a foreign matter particle and an extremely great difference occurs in quantity of light received between the shaded elements and the unshaded elements. For instance, a light sensitive area of $100\mu \times 100\mu$ square will be completely shaded by a particle of about $100\mu \times 100\mu$ size, and sensitive detection will be accomplished. However, a long and narrow foreign matter, say $50\mu \times 200\mu$ in size, will not cover the square light sensitive surface completely, although the projected area is the same. Therefore, such a foreign matter may not be detected.

Another conventional method that detects diffused reflection from foreign matters cannot discriminate foreign matters of different sizes because the ratio of reflection varies depending on the kinds of foreign matters.

In the present invention which has been made to overcome the above-mentioned drawbacks, the light sensitive surface of the light detector is divided into a multiplicity of small sections measuring 0.01 mm$^2$ to 1 mm$^2$ so that each light sensitive element generates an output signal proportional in magnitude to the projected area of foreign matters, and detection is accomplished by comparing the output signal with the reference value.

Foreign matters vary in shape, and typical shapes are particle and fiber. Foreign matters of fibrous shape generally measure $20\mu$ in diameter and more than ten times the diameter in length. Thus, a particle measuring $100\mu \times 100\mu$ has the same projected area as a fiber measuring $20\mu \times 500\mu$. If the limit of detection is to be set up for particles measuring $100\mu \times 100\mu$ and fibers measuring $20\mu$ in diameter (or $500\mu$ in length), the light sensitive surface of the detector should be divided into sections measuring $500\mu \times 500\mu$ (0.25 mm$^2$). By measuring the quantity of received light with each section of the divided light sensitive surface, it is possible to obtain an output signal proportional to the projected area of foreign matter regardless of its shape—particle, fiber, and others, and to obtain output signals having a sufficient S/N ratio, without mistaken detection due to small particles inherent to medical fluids.

According to a preferred embodiment of this invention, the light sensitive surface of the light detector is provided with a bundle of optical fibers connected to photoelectric elements in such a manner that each divided section of the light sensitive surface corresponds to each photoelectric element. Thus, the individual sections of the light sensitive surface are substantially continuous and there is no dead zone which might result in failure of detection.

In addition, photoelectric converting elements such as phototransistors, photodiodes, and photocells may be staggered directly on the light sensitive surface without using optical fibers, so that foreign matters suspended in the swirling liquid are detected by either row of the detecting elements. Such arrangement eliminates any dead zone.

In continuous and automatic detection the visual field of detection should be changed according to the size of ampoules to be tested, and this is accomplished by replacing the light receiver or by covering optically or mechanically a part of the light receiver. Such operation, however, needs skill, and a simple and certain method has been searched for.

According to the present invention the visual field for detection is changed as follows: The output signals from the group of small light sensitive elements are compared with the preset reference values to produce an output. Thus obtained output is then introduced into the detection visual field selector circuit that controls the number of small light sensitive elements to be used according to the size of objects to be detected.

The detection visual field selector circuit is a circuit to select a proper number of small light sensitive elements to be used according to the change of visual field relative to the size of objects to be detected. More particularly, it is so designed as to make presetting by means of a selector circuit according to the size of objects to be detected so that the number of small light sensitive elements to be used corresponds to the size of detection visual field. This is accomplished by the built-in matrix circuit such as diode matrix circuit and wired OR-circuit. Thus, it is possible to obtain by simple operation necessary and sufficient outputs from the output signals generated by the small light sensitive elements through the comparators. And the visual field thus changed is extremely accurate.

OBJECTS OF THE INVENTION

It is an object of the invention to provide a method to detect sensitively and easily foreign matters based on their projected areas regardless of their configuration.

Another object of the invention is to provide an apparatus which has no dead zone in the light sensitive area of the light detector.

A further object of the invention is to provide an apparatus to change simply and accurately the detection visual field according to the size of objects to be detected.

Other and further objects and features of the invention will be apparent from the following description taken in connection with the accompanying drawings.

BRIEF DESCRIPTION OF THE DRAWING

FIG. 7b is a block diagram to illustrate the action of the arrangement as shown in FIG. 7a.

DETAILED DESCRIPTION

Figure 1:
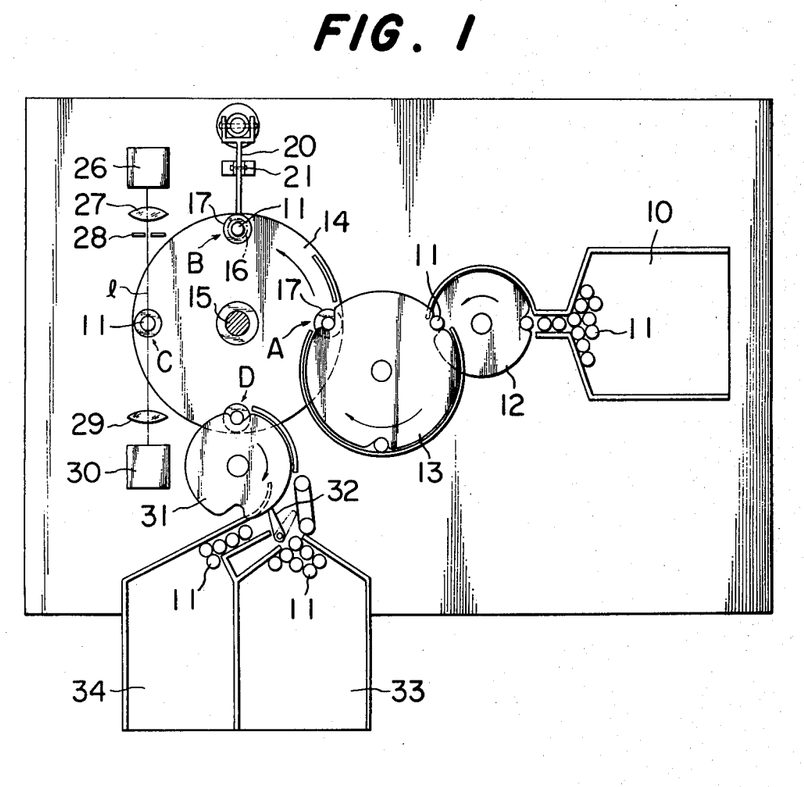
FIG. 1 is a plan view of apparatus suitable for carrying out several embodiments of the present invention.
Figure 2:
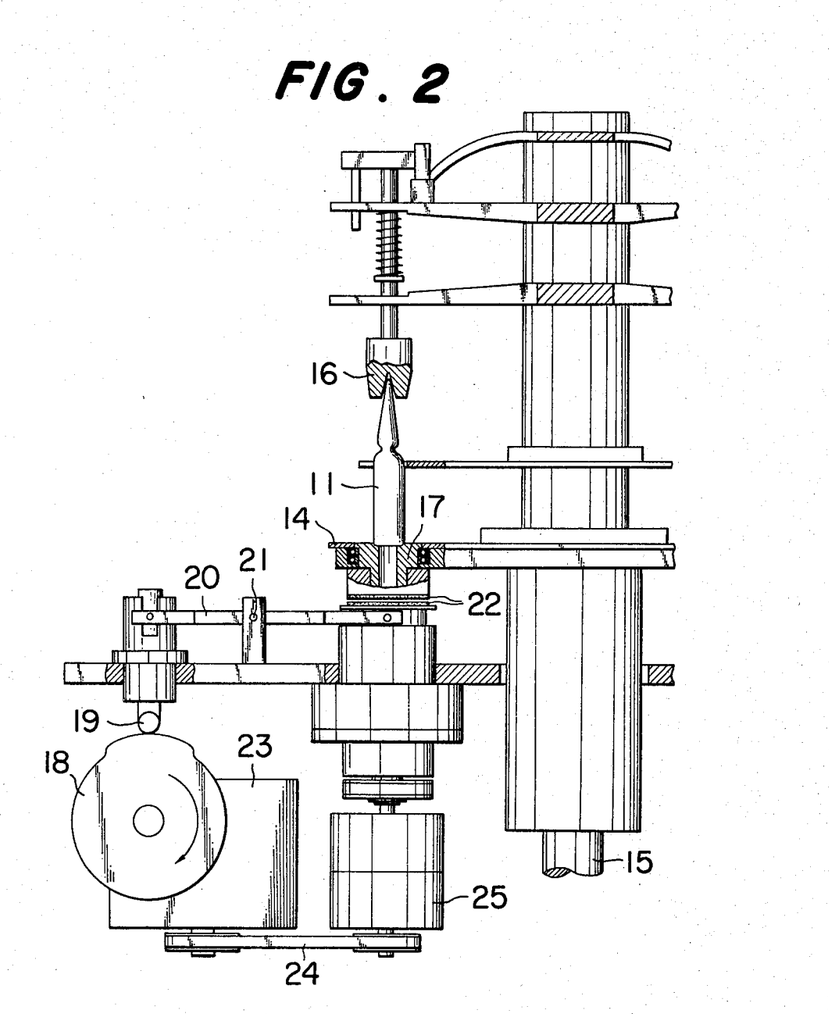
FIG. 2 is an enlarged sectional view of the turntable in FIG. 1.

Apparatus suitable for carrying out several embodiments of the present invention is described referring to FIGS. 1 and 2, wherein there is shown a hopper (10). Ampoules (11), which are objects to be detected, stored in the hopper (10) are fed one by one intermittently to a turntable (14) by feed star wheels (12) and (13) which mesh each other. The turntable (14) rotates intermittently by 90 degrees together with a head pressing cap (16) about the axis of rotation (15).

At position A, as the ampoule (11) is fed to a rotating seat (17) on the turntable (14), the head pressing cap (16) comes down to hold the ampoule (11). As the ampoule (11) is transferred to position B, a cam (18) rotates and a roller (19) goes down to actuate an arm (20) about a fulcrum (20), causing a disk clutch (22) to be engaged by a leaf spring (not shown) and connected to the rotating seat (17). Thus, the rotation of a motor (23) is transmitted through a belt (24) to turn the ampoule at a high speed. As the cam (18) rotates further to lift the roller (19), the clutch (22) is disengaged and, at the same time, a brake (25) is applied to stop rotation quickly. Subsequently, the ampoule (11) is transferred to detection position C by the intermittent rotation of the turntable (14).

At position C, the ampoule (11) is at a standstill, but the liquid and foreign matters in it continue to rotate. The ampoule (11) is illuminated by light (1) emitted from a light source (26) through a condenser lens (27) and a slit (28). The beam of light which has passed the liquid is focussed by a focussing lens (29) on a photodetector (30) which is described later. The photodetector (30) issues an output signal which is delayed for a prescribed time by a delay circuit and then actuates a solenoid for selection. As the ampoule (11), which has undergone detection, is further brought by intermittent rotation of the turntable (14) to position D, the head pressing cap (16) lifts and disengages. Thus, the ampoule (11) is discharged from the turntable (14) by a discharge wheel (31) of the selector unit. A selector lever (32) is flipped by the solenoid actuated according to the selection signal, and the ampoule (11) is received in a reject hopper (33) or acceptance hopper (34).

Figure 3:
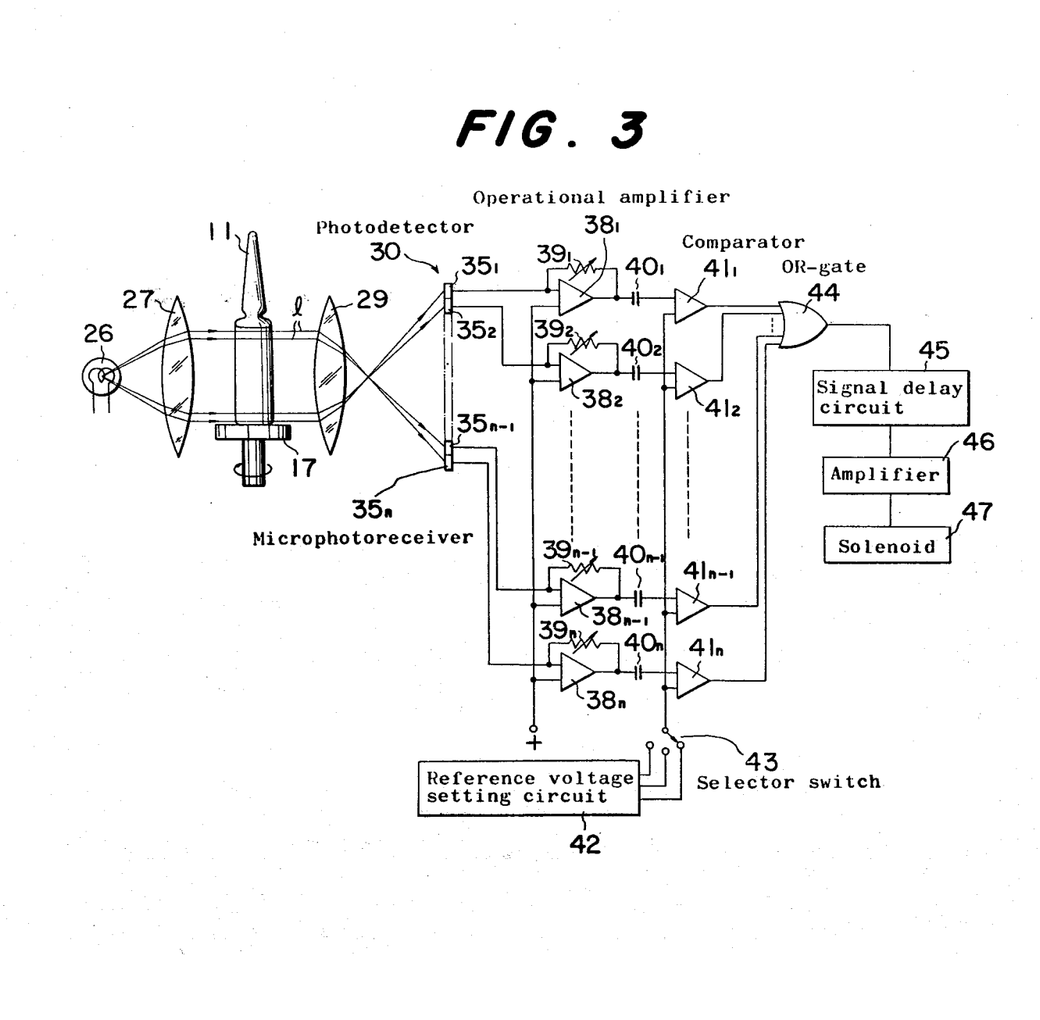
FIG. 3 is a block diagram to illustrate the operation of the apparatus according to the invention.
Figure 4A:
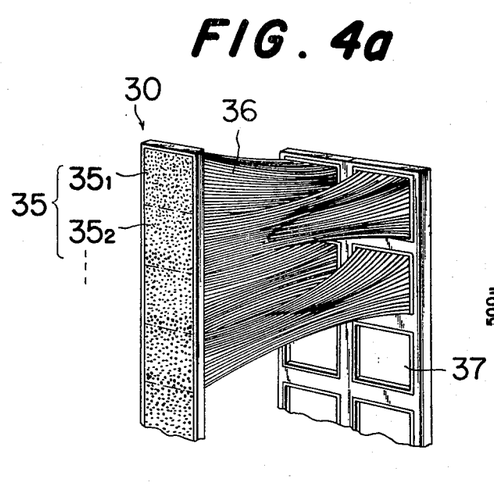
FIGS. 4a and 4b are perspective views of different examples of the light detector.
Figure 4B:
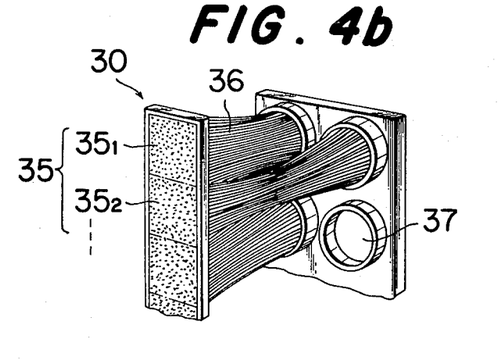

We will describe below the above-mentioned detecting device and the computing and processing circuit connected thereto referring to FIGS. 3, 4a, and 4b, wherein there are shown the light source (26), the condenser lens (27), the ampoule (11), the rotating seat (17), the focusing lens (29), and the photodetector (30). The light sensitive surface of the photodetector (30) consists of microphotoreceivers (35) of prescribed area arranged vertically. More particularly, optical fibers (36) about $10\mu$ in diameter are bundled in such a manner that their ends form the light receiving surface in the vertical frame of $500\mu$ width, as shown in FIG. 4a. The bundle of the optical fibers is divided at intervals of $500\mu$ so that the microphotoreceivers (35), each of which has an area of $500\mu \times 500\mu = 0.25$ mm$^2$, are formed. The bundle of optical fibers (36) forming the microphotoreceiver (35) is optically connected to photoelectric elements (37). The optical fibers are made of glass fibers, and the photoelectric elements are selected from phototransistors, photodiodes, and photocells. The shape may be square as shown in FIG. 4a or circular as shown in FIG. 4b.

The number of the microphotoreceivers (35) to be arranged vertically is determined so that the detection visual field covers the height from the liquid surface to the bottom of the ampoule (11). For instance, if 2-ml ampoules having detection visual field of 25 mm are to be detected, the bundle of the optical fibers (36) should be divided into 50 sections, each measuring $500\mu$, so that 50 units of microphotoreceivers (35) are arranged vertically.

In the above-mentioned example, 50 units of microphotoreceivers (35), each measuring 0.25 mm$^2$, are arranged vertically. However, for detection of ampoules of 1 ml to about 20 ml, it is desirable to arrange 20 to 120 units of microphotoreceivers (35), each measuring 0.01 mm$^2$ to 1 mm$^2$ in area. It goes without saying that a greater number of microphotoreceivers (35) should be used for detection of vials as large as 500 ml. There is substantially no boundary that makes a dead zone between any two microphotoreceivers (35), and this eliminates failure of detection.

The output signals from the photoelectric elements (37) are applied to the corresponding operational amplifiers $(38_1)$, $(38_2)$ ... $(38_n)$, which are of differential input type having variable resistors $(39_1)$, $(39_2)$ ... $(39_n)$ connected thereto to make uniform their DC output level when there is variation in sensitivity among the photoelectric elements (37). The output signals from the operational amplifiers $(38_1)$, $(38_2)$ ... $(38_n)$ have their DC components removed by capacitors $(40_1)$, $(40_2)$ ... $(40_n)$ that block the flow of direct current but permit the AC components to pass which are generated only when there are foreign matters in proportion to the size of the foreign matters. Such AC components pass through the capacitors and reach comparators $(41_1)$, $(41_2)$ ... $(41_n)$, to which are applied a reference voltage for comparison from a reference voltage setting circuit (42) through a selector switch (43) so that outputs are generated from the comparators only when the signal voltage from the capacitors (40₁), (40₂) ... (40ₙ) is greater than the reference voltage from the setting circuit (42). The reference voltage for comparison can be switched in multiple steps by means of the selector switch (43). The lower the reference voltage, the higher the sensitivity for detecting foreign matters of smaller size. Conversely, the higher the reference voltage, the lower the sensitivity for detecting foreign matters. The reference voltage can be changed by the selector switch (43) and also by the variable resistor continuously.

The output signals from the comparators ($41_1$), ($41_2$) ... ($41_n$) are applied to an OR-gate which gives a defective detection signal when any one of the comparators issues a detection signal for foreign matters. The defective detection signal is applied to a solenoid (47) through a signal delay circuit (45) and an amplifier (46) so that the selector lever (32) in FIG. 1 is flipped in either direction to select defective ampoules. The selector lever may be actuated by a proper electro-mechanical force converter such as an air valve and electromagnetic clutch.

In experiments with an embodiment in which the light sensitive surface of the photodetector (30) is divided into sections of microphotoreceivers (35), each measuring $500\mu \times 500\mu$, the detection result as shown in Table 1 was obtained.

Samples to be judged as acceptable are designated as group A ($A_1$ and $A_2$), and samples to be judged as defective are designated as group B ($B_1$ and $B_2$). The rate of detection is defined as the rate of samples which were judged as defective.

|  | Projected area | Shape |
|---|---|---|
| Group A |  |  |
| $A_1$ | $0.4 \times 10^3 (\mu^2)$ or less | $20\mu \times 20\mu$ or less |
| $A_2$ | $0.4 \times 10^3 (\mu^2)$ | $20\mu \times 20\mu$ |
| Group B |  |  |
| $B_1$ | $10 \times 10^3 (\mu^2)$ | $20\mu \times 500\mu$ |
| $B_2$ | $10 \times 10^3 (\mu^2)$ | $100\mu \times 100\mu$ |

TABLE 1

| Sample | Detection Rate (%) |
|---|---|
| $A_1$ | 0 |
| $A_2$ | 0 |
| $B_1$ | 99.5 |
| $B_2$ | 99.9 |

On the other hand, the following results were obtained when a 1024-bit self-scanning diode array in which 1024 units of light sensitive elements measuring $25.4\mu \times 12.7\mu$ are arranged at intervals of $12.7\mu$ was used as the photodetector and when the light sensitive surface divided into five sections measuring 5 mm=5 mm was used as shown in FIGS. 4a and 4b.

TABLE 2

| Light sensitive elements Sensitivity | Detection Rate | | | |
|---|---|---|---|---|
| | Diode array | | 5 mm × 5 mm elements | |
| | Low | High | Low | High |
| Samples | | | | |
| $A_1$ | 0.5% | 50% | 0% | 30% |
| $A_2$ | 0.9% | 70% | 0% | 33% |
| $B_1$ | 61% | 98% | 13% | 50% |

TABLE 2-continued

| Light sensitive elements Sensitivity | Detection Rate | | | |
|---|---|---|---|---|
| | Diode array | | 5 mm × 5 mm elements | |
| | Low | High | Low | High |
| $B_2$ | 75% | 99% | 15% | 55% |

Low level: less than 1% for group A
High Level: more than 90% for group B

As shown in Table 2, in the case where a diode array was used, if the detection rate for group A is held below 1%, the detection rate for group B is decreased to about 70%, and if the detection rate for group B is held above 90%, the detection rate for group A is increased to 50–70%. However, in the case where a little greater light sensitive elements were used, the sensitivity is insufficient and group A and group B are not separated completely.

In contrast to this, the method according to the present invention provides sure separation of group A and group B as shown in Table 1.

The limit for separation can be adjusted in a small range by varying the reference voltage for comparison. Adjustment to a large extent can be made by selecting an optimum light receiving area for each section of the microphotoreceivers (35) consitituting the photodetector (30) in the range of 0.01 mm² to 1 mm². It is also possible to set the relative ratio of the projected area of foreign matters to the microphotoreceivers (35) in the same manner as mentioned above by changing the magnification of the focussing lens (29). More simply, it is possible to change the sensitivity level by placing a shading mask on one part of the microphotoreceivers (35), although the linearity of output signals with respect to foreign matters is decreased. In this case the shading mask may be placed in front of the focussing lens, but preferably it should be placed in front of the microphotoreceivers (35) so that a sharp image is formed on the light sinsitive surface.

Figure 5:
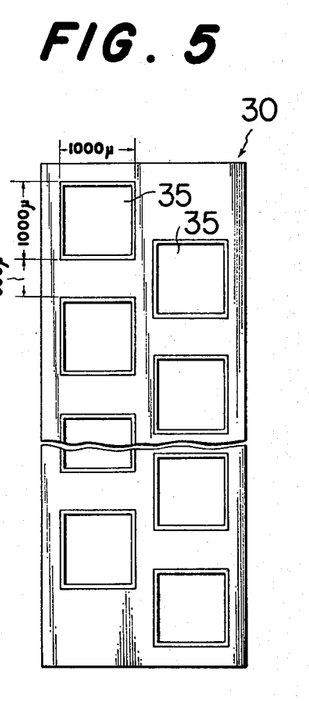
FIG. 5 is a front view of another example of the light detector.

FIG. 5 illustrates another embodiment of this invention in which light is received directly by the photodetector without using optical fibers. Square phototransistors measuring 1 mm×1 mm are used as the microphotoreceivers (35) constituting the photodetector (30). The phototransistors are spaced at intervals of 0.5 mm and one row is displaced by half a pitch from another row, so that an image of foreign matter of fibrous shape measuring $20\mu \times 500\mu$ will be caught by one section in either row. This eliminates failure of detection due to dead zone between elements. Thus, this embodiment provides the same result as was obtained with the embodiment in which optical fibers are used as shown in FIGS. 4a and 4b. Foreign matters of fibrous shape give various projected images depending on their movement. Therefore, the projected area of foreign matters varies if each section of the microphotoreceivers (35) is of rectangular shape having extremely different side lengths. However, if each unit of the microphotoreceivers is of square shape, it is possible to measure the size of foreign matters accurately because the entire projected image is given regardless of position of fibrous foreign matters. Thus, each unit should preferably be square.

Figure 6:
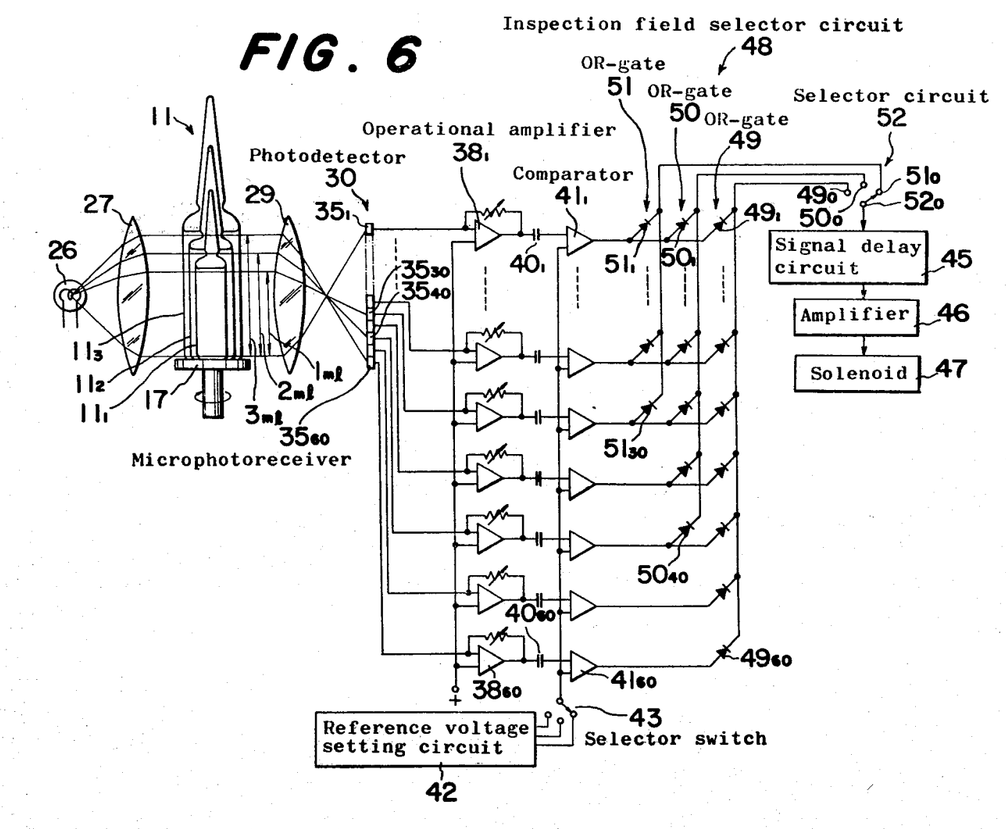
FIG. 6 is a block diagram to illustrate the apparatus according to the invention which is provided with a detection visual field selector circuit.

Referring to FIG. 6, we will describe the operating and processing circuit provided with the detection visual field selector circuit to change the detection visual field according to the size of ampoules to be inspected. In FIG. 6, there are shown the light source (26), the condenser lens (27), ampoules of different sizes ($11_1$), ($11_2$), ($11_3$), the focussing lens (29), and the photodetector (30). The light sensitive surface of the photodetector (30) consists of a multiplicity of the microphotoreceivers (35) arranged in one or more rows. The number of units to be arranged vertically is determined according to the maximum size of ampoules to be inspected. For inspection of ampoules ($11_1$), ($11_2$), ($11_3$) of 1 ml, 2 ml, and 3 ml, 60 units are arranged vertically so that the range from the liquid surface to the bottom of the 3-ml ampoule ($11_3$) is covered, and 40 units cover the 2-ml ampoule ($11_2$) and 30 units cover the 1-ml ampoule ($11_1$). The microphotoreceivers ($35_1$), ($35_2$) . . . ($35_{60}$) are connected to the corresponding photoelectric elements ($37_1$), ($37_2$) . . . ($37_{60}$), the operational amplifiers ($38_1$), ($38_2$) . . . ($38_{60}$), the capacitors ($40_1$), ($40_2$) . . . ($40_{60}$), and the comparators ($41_1$), ($41_2$) . . . ($41_{60}$) consecutively. The output signals from the comparators ($41_1$), ($41_2$) . . . ($41_{60}$) are applied to the inspection visual field selector circuit (48) which is made up of diode matrix circuits so that a number of the microphotoreceivers ($35_1$), ($35_2$) . . . ($35_{60}$) to be employed as the inspection visual field is changed according to the size of ampoules (11) to be inspected, is controlled. For inspection of 3-ml ampoules ($11_3$) all of 60 microphotoreceivers ($35_1$), ($35_2$) . . . ($35_{60}$) are used and the OR-gate (49) consisting of diodes ($49_1$), ($49_2$) . . . ($49_{60}$) is connected. Similarly, for inspection of 2-ml ampoules ($11_2$) the OR-gate (50) consisting of diodes ($50_1$), ($50_2$) . . . ($50_{40}$) is connected to 40 microphotoreceivers ($35_1$), ($35_2$) . . . ($35_{40}$). Further, for inspection of 1-ml ampoules ($11_1$), the OR-gate (51) consisting of diodes ($51_1$), ($51_2$) . . . ($51_{30}$) is connected to 30 microphotoreceivers ($35_1$), ($35_2$) . . . ($35_{30}$). The respective OR-gates (49), (50), and (51) are connected to the delay circuit (45), the amplifier (46), and the solenoid (47), as in FIG. 3, through the selector circuit (52) having terminals ($49_0$), ($50_0$), ($51_0$), and ($52_0$).

For inspection of 3-ml ampoules ($11_3$) the common terminal ($52_0$) of the selector circuit (52) is connected to the terminal ($49_0$) of the OR-gate (49) and output signals from all of 60 microphotoreceivers ($35_1$), ($35_2$) . . . ($35_{60}$) function effectively. Thus, the inspection visual field selector circuit (48) issues outputs regardless of signals for detection of defectives. Likewise, for inspection of 2-ml ampoules ($11_2$) the common terminal ($52_0$) of the selector circuit (52) is connected to the terminal ($50_0$) of the OR-gate (50) and output signals from 40 microphotoreceivers ($35_1$), ($35_2$) . . . ($35_{40}$) function effectively, with output signals from the remaining 20 microphotoreceivers ($35_{41}$) . . . ($35_{60}$) being cut off. For inspection of 1-ml ampoules ($11_1$), output signals from 30 microphotoreceivers ($35_1$), ($35_2$) . . . ($35_{30}$) function effectively, with the remaining output signals being cut off. Thus, it is possible to change easily and accurately without any skill the inspection visual field by switching operation of the selector circuit (52) alone. It is expected that the present invention will improve the accuracy and efficiency of selection in the automatic inspection apparatus of this kind.

In FIG. 6 which illustrates inspection of ampoules of 1 ml, 2 ml, and 3 ml sizes the inspection visual field selector circuit (48) and the selector circuit (52) are designed for switching for these three sizes. However, it should be understood that modification can be made easily so that switching is accomplished according to various sizes of ampoules.

Figure 7A:
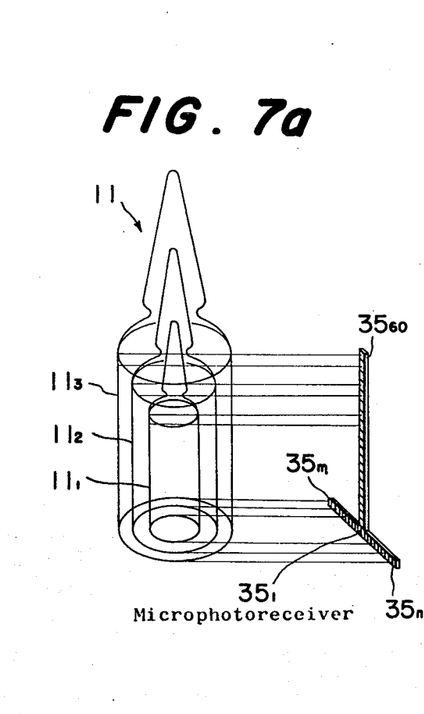
FIG. 7a is a perspective view of an example in which the light detector is arranged not only in vertical direction but in horizontal direction corresponding to the bottom of ampoules to be detected.
Figure 7B:
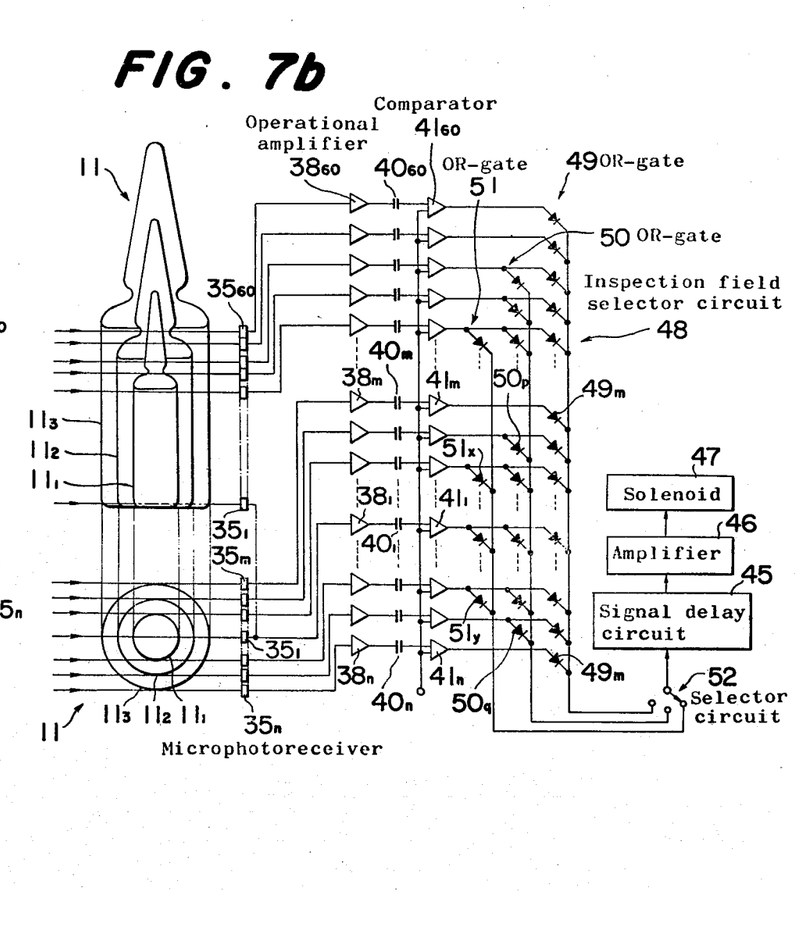

In the embodiment as shown in FIG. 6 the microphotoreceivers ($35_1$), ($35_2$) . . . ($35_{60}$) are arranged vertically. In FIG. 7a the microphotoreceivers are arranged horizontally at the position corresponding to the bottom of the ampoule, in addition to the vertically arranged ones. Such arrangement will permit complete detection of heavy foreign matters such as glass chips that tend to settle on the bottom. In FIG. 7a the microphotoreceivers ($35_1$), ($35_2$) . . . ($35_{60}$) are arranged vertically in one or more rows along the approximate center line of the ampoule (11) and the microphotoreceivers ($35_m$) . . . ($35_1$) . . . ($35_n$) are arranged horizontally in one or more rows along the bottom of the ampoule (11). As shown in FIG. 7b the horizontally arranged microphotoreceivers ($35_m$) . . . ($35_1$) . . . ($35_n$) are connected through respective photoelectric elements to the operational amplifiers ($38_m$) . . . ($38_1$) . . . ($38_n$), the capacitors ($40_m$) . . . ($40_1$) . . . ($40_n$), and the comparators ($41_m$) . . . ($41_1$) . . . ($41_n$). To the output side of these comparators are connected the diode array ($49_m$) . . . ($49_n$), ($50_p$) . . . ($50_q$), and ($51_x$) . . . ($51_y$) corresponding to the widths of ampoules ($11_3$), ($11_2$), and ($11_1$). These diodes, together with the diodes for the vertical row, constitute the inspection visual field selector circuit (48).

In such construction, it is possible to change the inspection visual field according to the width of ampoules as well as the height of ampoules, by switching the OR-gates (49), (50), and (51) through the selector circuit (52). Thus, heavy foreign matters such as glass chips that tend to settle on the bottom of the ampolue can be detected completely.

Instead of the matrix circuits constituting the visual field selector circuit (48), wired OR-circuits can be used for the same effect.

In the above-mentioned embodiment the inspection visual fields for the vertical row and horizontal row are switched synchronously, but a different arrangement is possible that permits separate switching of the vertical row and horizontal row. Such arrangement will permit inspection of more different sizes of ampoules.

What is claimed is:

1. An apparatus including a photodetector and of the type for detecting foreign matters in liquids by the steps of turning a transparent container filled with a liquid at high speed, bringing the container to a standstill and therewith permitting foreign suspended matters to swirl within the liquid, illuminating the liquid and foreign matters and therewith causing the transmitted light to be received by the light sensitive surface of the photodetector opposed to the container, and measuring the quantity of light received, said apparatus including the improvement comprises in that said light sensitive surface is divided along its length into a row of sections eachconstituting a microphotoreceiver including a photoelectric element, a multiplicity of operational amplifiers of differential input type having variable resistors connected thereto to make uniform their DC output level despite variations in sensitivity among the photoelectric elements, and each having a signal input driven by its own one of said microphotoreceivers, capacitors in series with the outputs of said operational amplifiers for removing DC components from said outputs but passing AC components proportional to the size of foreign matters passing in front of the corresponding microphotoreceiver, a comparator for each microphotoreceiver, said comparators each having one input driven thereby through the corresponding said operational amplifier and capacitor, each said comparator having a reference signal input, means for applying a reference signal to said reference signal inputs, at least one inspection field selection circuit having its inputs respectively connected to the outputs of the comparators for a desired portion of said row of mirophotoreceivers, and output circuit means actuable by an output from said inspection field selection circuit to indicate an unsatisfactory foreign matters condition in a container being inspected, said reference signal applying means including a selector switch and a plurality of different reference voltage terminals individually selectable by said switch for application of reference signals to the reference input of said comparator of several magnitudes dependent on several minimum sizes of foreign matters to be detected;

wherein one portion of said microphotoreceivers is arranged in one or more rows extending vertically to the maximum effective height of the containers to be inspected and a further portion of said microphotoreceivers is arranged in one or more rows extending horizontally to the maximum effective width of the containers to be inspected and visually opposed to the bottom portion of the containers, a said inspection field selection circuit being connected to the outputs of a group of microphotoreceivers including both a vertical row and a horizontal row of microphotoreceivers which vertical and horizontal rows correspond in length respectively to the height and diameter of the containers to be inspected, said inspection field selection circuit comprising diode matrix circuits which are built so that the number of the microphotoreceivers to be employed is changed according to the size of the transparent container, said diode matrix circuits including a first set of diodes respectively connecting the outputs of corresponding ones of a first set of said comparators to a first alternately selectable input of said selection circuit, a second set of diodes respectively connecting the outputs of only a portion of said comparators of said first set to a second alternately selectable input of said selection circuit, a third set of diodes respectively connecting the outputs of only part of said portion of said comparators of said first set to a third alternatively selectable input of said selection circuit, said first, second and third sets of diodes serving at least one vertical row of microphotoreceivers;

fourth, fifth and sixth sets of diodes connected like said first, second and third sets but with their inputs fed by further comparators serving at least one said horizontal row of microphotoreceivers;

first, second and third output lines alternatively connecting said inspection field selection circuit to said output circuit through alternative selection means, the outputs of said first and fourth diode sets connecting to said first output line, the outputs of said second and fifth diode sets connecting to said second output line, and the outputs of said third and sixth diode sets connecting to said third output line.

2. An apparatus for detecting foreign matters in liquids as claimed in claim 1 including photoelectric converting elements and optical fibers feeding the light beam received by the microphotoreceivers of the light sensitive surface to corresponding photoelectric converting elements, at least two rows of said photoelectric elements being fed by a single row of microphotoreceivers, corresponding photoelectric elements in said two rows being located substantialy side-by-side, with individual bundles of said optical fibers connecting alternate microphotoreceivers to respective photoelectric elements in one row and the remaining microphotoreceivers to respective photoelectric elements in the other row with said bundles partly twisted around each other so that vertically adjacent microphotoreceivers connect to horizontaloy or diagonally opposed photoelectric elements.

3. An apparatus for detecting foreign matters in liquids as claimed in claim 1 wherein the microphotoreceivers of the light sensitive surface lie parallel with the transparent container, the microphotoreceivers being staggered with some overlapping in the direction perpendicular to the revolving axis of the transparent container so that there is no dead zone.

* * * * *